United States Patent [19]

Goddard

[11] Patent Number: 5,224,943
[45] Date of Patent: Jul. 6, 1993

[54] CRYOSURGICAL APPARATUS

[75] Inventor: Robert W. Goddard, Andover, Great Britain

[73] Assignee: Spembly Medical Ltd., Andover, United Kingdom

[21] Appl. No.: 689,894

[22] PCT Filed: Dec. 14, 1989

[86] PCT No.: PCT/GB89/01548
§ 371 Date: Jul. 19, 1991
§ 102(e) Date: Jul. 19, 1991

[87] PCT Pub. No.: WO90/06726
PCT Pub. Date: Jun. 28, 1990

[30] Foreign Application Priority Data

Dec. 17, 1988 [GB] United Kingdom ............... 8829525

[51] Int. Cl.$^5$ .............................................. A61B 17/36
[52] U.S. Cl. ...................... 606/20; 606/22; 606/23
[58] Field of Search ........................... 606/20-26

[56] References Cited

U.S. PATENT DOCUMENTS

| Re. 28,657 | 12/1975 | Barger et al. | 606/23 |
| 3,524,446 | 8/1970 | Crump et al. | 606/25 |
| 3,794,039 | 2/1974 | Kollner et al. | 606/22 |
| 3,913,581 | 10/1975 | Ritson et al. | 606/23 |
| 3,993,075 | 11/1976 | Lisenbee et al. | 606/25 |
| 4,018,227 | 4/1977 | Wallach | 606/23 |
| 4,206,760 | 6/1980 | Davis | 606/23 |
| 4,275,734 | 6/1981 | Mitchiner | 606/23 |
| 4,377,168 | 3/1983 | Rzasa et al. | 606/24 |

*Primary Examiner*—Peter A. Aschenbrenner
*Attorney, Agent, or Firm*—Stanley J. Price, Jr.

[57] ABSTRACT

A cryosurgical probe for freezing human or animal tissue in a surgical procedure utilising the Joule Thomson effect. The probe is provided with a valve arrangement which enables selective purging and freezing cycles to be employed in rapid succession, and remote from the Joule-Thomson nozzle. In this way purging is limited to those parts of the probe which are affected by moisture contamination during the normal pre-sterilising process, and without interference with the Joule-Thomson nozzle.

5 Claims, 2 Drawing Sheets

CRYOSURGICAL APPARATUS

FIELD OF THE INVENTION

The present invention relates to cryosurgical apparatus and in particular to a cryoprobe for freezing human or animal tissue in a surgical procedure.

BACKGROUND OF THE INVENTION

Most cryosurgical probes in use today are cooled by expanding a gas at high pressure in a cavity at the working tip of the probes whereby in accordance with the Joule-Thomson effect, the gas undergoes rapid cooling and the tip is brought quickly to its operating temperature.

Before using a cryosurgical probe of this type it has to be sterilised by a steam process. In this process probe moisture contamination may occur which will either prevent the probe from functioning at all or cause the tip to defrost after a short period of time by clogging the gas flow passages and the Joule Thomson nozzle through which the gas is caused to expand into the tip cavity.

It is normal practice therefore to purge the gas flow passages and Joule-Thomson nozzle of moisture contamination subsequent to the steam sterilisation process, by a purging method which involves passing a low pressure dry gas of the type eventually used for the cooling process, but at a higher pressure, through the probe gas flow passageways including the Joule-Thomson nozzle.

However for small diameter probes the required purging time is unacceptably high which reduces the efficiency of the device in the hands of the surgeon primarily because of the waiting time before it can be used.

Attempts have been made to reduce the purging time. For example, one method entails passing a low pressure gas through the probe in a flow direction reverse to the normal flow direction to effect cooling, i.e. the probe freeze cycle, and increasing the flow rate by drilling two small by-pass holes near the Joule-Thomson nozzle.

An alternative method disclosed in U.S. Pat. No. 3,613,689 utilises a valve which closes a by-pass hole provided close to the Joule-Thompson nozzle under the effect of high-pressure gas flow in the probe freeze cycle, but which is constrained to move away from the by-pass hole under the effect of low pressure gas during the probe purge cycle or warming mode, so increasing the flow rate and consequently the purging time. In this design the gas flow direction in both the purge and freeze cycles is the same.

The increased purging time provided by the prior art is, however, still not short enough fully to satisfy operational requirements. Moreover the introduction of small holes in the vicinity of the Joule-Thomson nozzle has the undesirable effect of decreasing the pressure drop across the nozzle so reducing its efficiency and the cooling effect.

SUMMARY OF THE INVENTION

It is an object of the present invention to solve the problems of the prior art above stated and to provide a cryosurgical probe which is capable of being purged of contaminating moisture to such rapid extent as to constitute an event which to all intents and purposes is unnoticed by the operator.

According to the invention there is provided a cryosurgical probe comprising a probe body, an operating tip at one end of the body, first and second passageways leading to and from a cavity in the probe tip, means for expanding a high pressure gas in said cavity delivered along said first passageway thereby to cool the gas and said tip, and valve means arranged in the probe body and selectively operable between a probe purge cycle position whereat to by-pass said expanding means and direct flow of a purging gas delivered along said second passageway to said first passageway, and a freeze cycle position whereat to direct a high pressure gas along said first passageway to said expanding means then to exhaust from said cavity after expansion, along said second passageway.

With this arrangement it is possible to purge the probe prior to a freezing sequence very rapidly compared with known techniques because purging may be limited to those parts of the probe which have been affected by moisture contamination during the sterilising process and it does not involve any modification of or interference with the means for expanding the refrigerant gas as with previous purging methods.

Moreover since the valve means is positioned in the probe body, better control of purging rate is possible and greater purge flow rates may be used leading to shorter purging times.

Other features and advantages of the invention will become apparent from the following description of a preferred embodiment of the invention illustrated in a number of accompanying drawings.

BRIEF DESCRIPTION OF THE DRAWINGS

The accompanying drawings may be described as follows.

BEST MODES OF CARRYING OUT THE INVENTION

Figure 1:
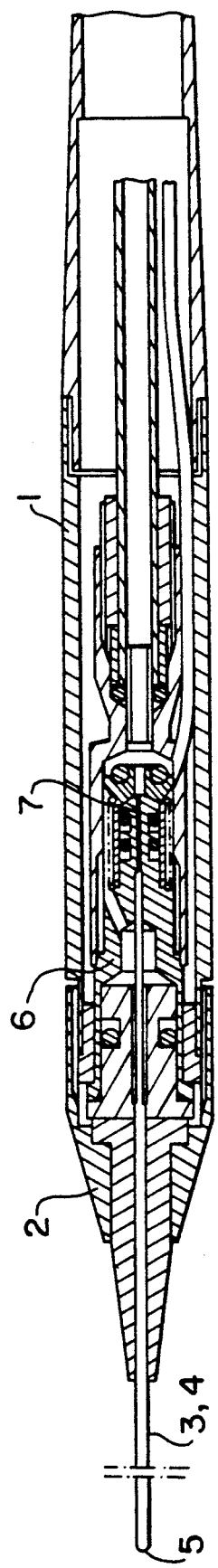
FIG. 1 shows a cross sectional view through a cryosurgical probe incorporating the invention.
Figure 2:
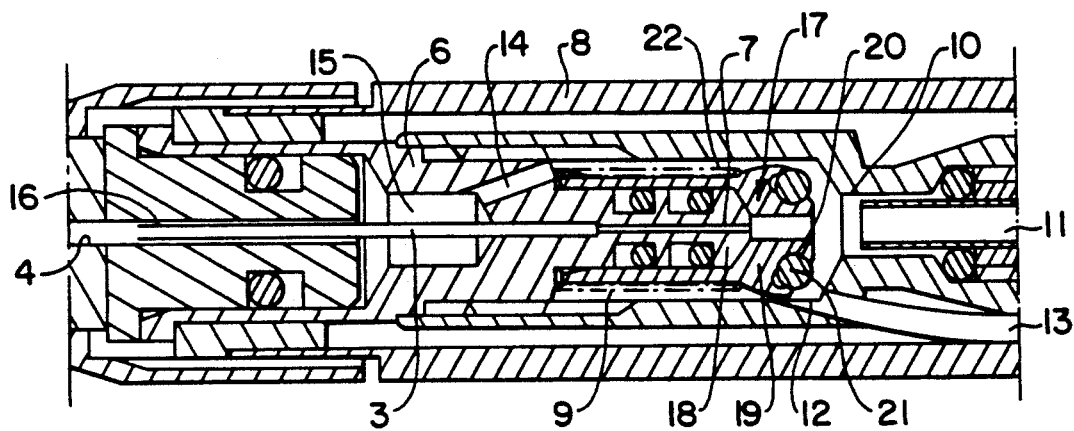
FIG. 2 is an enlarged cross sectional view of a part of the probe of FIG. 1 and showing detail of the valve means thereof in a probe purge cycle position.

The cryosurgical probe shown in the drawings comprises a probe body 1, constituting the handle of the probe, provided with a nose piece 2.

A pair of co-axially mounted hypodermic tubes 3, 4 extend from the nose piece 2 to form an operating probe tip 5, and communicate with the interior of the probe body 1.

The inner tube 3 terminates interiorly of the probe body 1 in a valve support block 6, along an axial extent thereof, to communicate with an axial bore 7 formed in the block 6.

The valve support block 6 is surrounded by a housing 8 forming a chamber 9 with the block 6.

The chamber 9 has a port 10 communicating with a passageway 11 extending axially of the probe body and a port 12 communicating with a passageway 13 extending along the probe body 1 adjacent the passageway 11.

A further port 14 leads from the chamber 9 to a second chamber 15 formed in the support block 6 and in communication with a passageway 16 formed between the inner and outer hypo tubes 3 and 4.

A valve actuator member 17 is mounted for slidable movement on a boss 18 formed on the valve support block 6.

The head 19 of the actuator member 17 is provided with sockets 20 containing valve sealing members 21.

Figure 3:
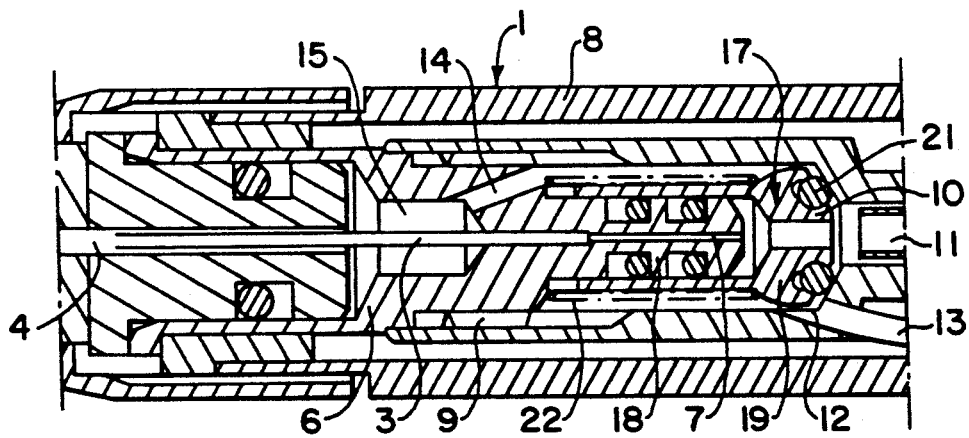
FIG. 3 is the same view as FIG. 2 but with the valve positioned in a probe freeze cycle.

The actuator member 17 is urged by a spring 22 to adopt a position, see FIG. 3, where the sealing members 21 abut the inner walls of the chamber 9 which corresponds to the occurrence of a probe freeze cycle when a gas at high pressure is delivered along the passageway 13, normally called the supply passageway, enters the chamber 9 through port 12, passes to the chamber 15 through port 14 and thence along the passageway 16 to the probe tip 5. The pressure created in the chamber 9 by the presence of operating gas in the freeze cycle ensures that the actuator member 17 remains in its normally closed position.

At the probe tip 5 the high pressure gas is caused to expand in a cavity (not shown) in the tip 5, by being passed through a restriction formed in the passageway 16. The tip 5 is thereby cooled.

The exhaust gas leaves the tip cavity via the inner hypo-tube 3 hence passing to the bore 7 in support block 6, through the port 10 in chamber 9 and along passageway 10, normally called the exhaust passageway, to exhaust.

Before the freeze cycle is initiated in a particular surgical procedure as explained earlier, the probe body 1 together with the flexible tubing connecting the body to the control console (not shown) has to be sterilised by a steam procedure. The resulting moisture contamination is removed by purging the passageways for inlet and exhaust operating gas, through the flexible tubing and probe body, using a low pressure gas delivered in a reverse mode to that of the freezing cycle.

Accordingly low pressure gas is delivered along passageway 11, and the resulting pressure build-up at the head of actuator member 17 at port 10 causes the sealing members 21 of the valve actuator member 17 to move away from their sealing positions and open port 10, allowing the purging gas to exit through port 12 and along passageway 13, the normal supply passageway for the operating gas.

When the purge flow is stopped by actuation of a purge valve in the operating console which may be by foot actuation, the valve actuator member 17 returns to its normal position under the action of return spring 22 allowing the freeze cycle to commence.

The design as above described provides a true end freeze cryosurgical probe in contrast to the prior art particularly that described in U.S. Pat. No. 3,613,689 above referred to.

This is essential in certain cryosurgical procedures and is made possible by virtue of creating a different flow path to and from the Joule-Thomson nozzle and by locating the valve for selecting the freeze and purge cycles in the probe body, normally the handle, and not at the tip.

In this way the use of a much larger valve is possible creating the facility for better overall control of probe purging with the consequent ability to provide rapid purging rates.

I claim:

1. A cryosurgical probe comprising,
   a probe body,
   an operating tip at one end of said body,
   first and second passageways leading to and from a cavity in said operating tip,
   means for expanding a high pressure gas in said cavity delivered along said first passageway to cool the gas and said tip,
   valve means positioned in said probe body for controlling gas flow between said first and second passageways,
   said valve means being selectively movable in said probe body to a first position in a probe purge cycle for bypassing said expanding means to direct flow of a purging gas delivered along said second passageway to said first passageway,
   said valve means being selectively movable in said probe body to a second position in a freeze cycle for sealing said first passageway from said second passageway to direct a high pressure gas along said first passageway to said expanding means and then exhaust the gas from said cavity after expansion through said second passageway.

2. A cryosurgical probe as set forth in claim 1 wherein,
   said valve means includes spring biasing means for maintaining said valve means in said freeze cycle position.

3. A cryosurgical probe as set forth in claim 2 which includes,
   a valve support block positioned within a chamber in said probe body,
   said valve means including a slidable actuator position on said valve support block, and
   said second passageway extending through said valve support block to said probe tip.

4. A cryosurgical probe as set forth in claim 3 in which,
   said chamber for high pressure gas passed along said second passageway is closed when said valve means is in said second position for the freeze cycle,
   said valve means being movable to said first position for said probe purge cycle against the action of said biasing means in response to pressure build-up of purging gas on said slidable actuator of the valve means, and
   said slidable actuator in said first position permitting purging gas to flow from said second passageway to said chamber during said probe purge cycle in the direction of said probe tip and thereafter to exit said chamber through said first passageway.

5. A cryosurgical probe as set forth in claim 4 wherein,
   said slidable actuator of said valve means includes sealing means for abutting the walls of said chamber in said second position of said valve means during said probe freeze cycle.

* * * * *